(12) United States Patent
Jensen et al.

(10) Patent No.: US 6,759,422 B2
(45) Date of Patent: Jul. 6, 2004

(54) ION CHANNEL MODULATING AGENTS

(75) Inventors: Bo Skaaning Jensen, Kobenhavn (DK); Lene Teuber, Vaerlose (DK); Dorte Strobaek, Farum (DK); Palle Christophersen, Ballerup (DK); Soren Peter Olesen, Klampenborg (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 10/210,043

(22) Filed: Aug. 2, 2002

(65) Prior Publication Data

US 2003/0008906 A1 Jan. 9, 2003

Related U.S. Application Data

(60) Division of application No. 09/986,677, filed on Nov. 9, 2001, now abandoned, application No. 09/986,677, which is a continuation-in-part of application No. PCT/DK00/00255, filed on May 12, 2000.

(30) Foreign Application Priority Data

May 12, 1999 (DK) ........................... 1999 00657

(51) Int. Cl.$^7$ ........................................... A61K 31/428
(52) U.S. Cl. ...................... 514/366; 514/367
(58) Field of Search .................. 514/366, 367

(56) References Cited

U.S. PATENT DOCUMENTS

| | | | |
|---|---|---|---|
| 1,787,315 A | 12/1930 | Kaufmann et al. | |
| 2,019,529 A | 11/1935 | Engelmann et al. | |
| 2,061,632 A | 11/1936 | Lenher | |
| 2,890,985 A | 6/1959 | Marsh et al. | |
| 3,094,462 A | 6/1963 | Gardocki et al. | |
| 4,929,623 A | 5/1990 | Abe et al. | |
| 4,971,983 A | * 11/1990 | Johnson et al. | 514/340 |
| 5,008,280 A | 4/1991 | Gueremy et al. | |
| 5,236,940 A | 8/1993 | Audiau et al. | |
| 5,567,822 A | 10/1996 | Audiau et al. | |
| 5,594,145 A | 1/1997 | Forstinger et al. | |

FOREIGN PATENT DOCUMENTS

| | | |
|---|---|---|
| DE | 271258 | 8/1989 |
| EP | 0 374 040 | 6/1990 |
| EP | 0 374 041 | 6/1990 |
| GB | 1 578 990 | 11/1980 |
| WO | WO 92/14731 | 9/1992 |
| WO | WO 98/40381 | 9/1998 |
| WO | WO 99/21541 | 5/1999 |

OTHER PUBLICATIONS

Chemical Abstracts, vol. 52, No. 6, 1958, Abstract No. 14697 (JP 32,009075 A, Oct. 24, 1957).
Hajduk et al., J. Med. Chem., 1999, 42 (19), 3852–3859.
Kajino et al., Chem. Pharm. Bull., 39(11) 2888–2895 (1991).
Inoue et al., Chem. Pharm. Bull., 45 (6) 1008–1026 (1997).
Opgenorth et al., CA 88:136609, 1978.
Inoue et al., CA 127:161810, 1997.
Kajino et al., CA 116:128835, 1992.
Machon et al., CA 64:6637a, 1996.
Todesco, CA 63:1323h, 1965.
Jung et al., CA 121:35597, 1994.
Matsumoto et al., CA 115:182322, 1991.
Matsumoto et al., CA 114:247193, 1991.
Saprykina et al., CA 107:7108, 1987.
Simov et al., CA 95:5940, 1981.
Papenfuhs, CA 93:168255, 1980.
Kato et al., CA 86:74195, 1977.
Hlavaty et al., CA 85:108128, 1976.
Pilgram et al., CA 81:169465, 1974.
Barnett, CA 81:13492, 1974.
Nishida et al., CA 80:134888, 1974.
Kumano et al., CA 80:38358, 1974.
Nishida et al., CA 78:17611, 1973.
Pawellek et al., CA 77:114392, 1972.
Nishida et al., CA 73:78523, 1970.
Grube et al., CA 71:21385, 1969.
Clark et al., CA 98:89352, 1983.
Schuster et al., CA 113:19438, 1990.

* cited by examiner

*Primary Examiner*—Laura L. Stockton
(74) *Attorney, Agent, or Firm*—Birch, Stewart, Kolasch & Birch, LLP

(57) ABSTRACT

The present invention relates to ion channel modulating agents. More particularly, the present invention relates to a particular class of chemical compounds represented by general formula (I) that has proven useful as modulators of $SK_{Ca}$, $IK_{Ca}$ and $BK_{Ca}$ channels. In further aspects, the present invention relates to the use of these SK/IK/BK channel modulating agents for the manufacture of medicaments and pharmaceutical compositions comprising the SK/IK/BK channel modulating agents. The SK/IK/BK channel modulating agents of the invention are useful for the treatment or alleviation of diseases and conditions associated with the SK/IK/BK channels.

12 Claims, No Drawings

ION CHANNEL MODULATING AGENTS

This application is a divisional of application Ser. No. 09/986,677, filed on Nov. 9, 2001, now abandoned, and for which priority is claimed under 35 U.S.C. § 120. Application Ser. No. 09/986,677 is a continuation of PCT International Application No. PCT/DK00/00255 filed on May 12, 2000. The entire contents of each of the above-identified applications are hereby incorporated by reference. This application also claims priority of Application No. PA 1999 00657 filed in Denmark on May 12, 1999 under 35 U.S.C. § 119.

TECHNICAL FIELD

The present invention relates to novel ion channel modulating agents. More particularly, the present invention relates to a particular class of chemical compounds that has proven useful as modulators of $SK_{Ca}$, $IK_{Ca}$ and $BK_{Ca}$ channels. In further aspects, the present invention relates to the use of these SK/IK/BK channel modulating agents for the manufacture of medicaments, and pharmaceutical compositions comprising the SK/IK/BK channel modulating agents.

The SK/IK/BK channel modulating agents of the invention are useful for the treatment or alleviation of diseases and conditions associated with the SK/IK/BK channels.

BACKGROUND ART

Ion channels are transmembrane proteins, which catalyse the transport of inorganic ions across cell membranes. The ion channels participate in processes as diverse as the generation and timing of action potentials, synaptic transmissions, secretion of hormones, contraction of muscles, etc.

Many drugs exert their effects via modulation of ion channels. Examples are anti-epileptic compounds like Phenytoin and Lamotrigine, which block voltage dependent $Na^+$-channels in the brain, anti-hypertensive drugs like Nifedipine and Diltiazem, which block voltage dependent $Ca^{2+}$-channels in smooth muscle cells, and stimulators of insulin release like Glibenclamide and Tolbutamide, which block an ATP-regulated $K^+$-channel in the pancreas.

All mammalian cells express potassium ($K^+$) channels in their cell membranes, and the channels play a dominant role in the regulation of the membrane potential. In nerve and muscle cells they regulate the frequency and form of the action potential, the release of neurotransmitters, and the degree of broncho- and vasodilation.

From a molecular point of view, the $K^+$ channels represent the largest and most diverse group of ion channels. For an overview they can be divided into five large subfamilies: Voltage-activated $K^+$ channels ($K_v$), long QT related $K^+$ channels (KvLQT), inward rectifiers ($K_{IR}$), two-pore $K^+$ channels ($K_{TP}$), and calcium-activated $K^+$ channels ($K_{Ca}$).

The latter group, the $Ca^{2+}$-activated $K^+$ channels, consists of three well-defined subtypes: SK channels, IK channels and BK channels. SK, IK and BK refer to the single-channel conductance (Small, Intermediate and Big conductance K channel). The SK, IK, and BK channels exhibit differences in e.g. voltage- and calcium-sensitivity, pharmacology, distribution and function.

$Ca^{2+}$-activated SK channels are present in many central neurons and ganglia, where their primary function is to hyperpolarize nerve cells following one or several action potentials to prevent long trains of epileptogenic activity to occur. The SK channels are also present in several peripheral cells including skeletal muscle, gland cells, liver cells, and T-lymphocytes.

The significance of SK channels in normal skeletal muscle is not clear, but their number is significantly increased in denervated muscle, and the large number of SK channels in the muscle of patients with myotonic muscle dystrophia suggest a role in the pathogenesis of the disease.

A number of blockers of SK channels exist, e.g. apamin, atracurium, pancuronium, and tubocurarine, and they are all positively charged molecules which act as pore blockers.

The $Ca^{2+}$-activated IK channel shares a number of characteristics with the $Ca^{2+}$-activated SK channel, since it is highly K-selective, is activated by sub-micromolar concentrations of $Ca^{2+}$, and has an inwardly rectifying conductance. However, there are also striking differences. The unit conductance of the IK channel is 4–5 fold higher than that of the SK channel, and the distribution of the IK channel is restricted to the blood and vasculature. Thus, the IK channel is not expressed in the nervous system and in muscle, but in endothelial cells, cells of epithelial origin and in red blood cells.

In the red blood cells, where the IK channel has been denominated the Gardos channel, a rise in the concentration of intracellular $Ca^{2+}$ opens the channel and causes potassium loss and cell dehydration, a condition which is exacerbated in sickle cell anemia. Promising therapeutic approaches for sickle cell anemia involve specific block of the IK channel.

IK channels have also been implicated in the microvasculature of the kidney, where they may be responsible for the vasodilatory effects of bradykinin. The decrease in blood pressure during septic shock is caused by an increased NO production by the endothelial cells, and the IK channels in these cells are responsible for maintaining the $Ca^{2+}$ influx activating the $Ca^{2+}$-sensitive NO-synthase.

In brain capillary endothelial cells, IK channels, activated by endothelin that is produced by neurons and glia, shunt excess $K^+$ into the blood. Neurotrophilic granulocytes, i.e. mobile phagocytic cells that defend the body against microbial invaders, undergo large depolarisation subsequent to agonistic stimulation, and IK channels have been implicated in depolarising the stimulated granulocyte.

The $Ca^{2+}$-activated BK channels present in many cells including most central and peripheral nerve cells, striated muscle cells, cardiac cells, smooth muscle cells of the airways, the vasculature, the gastrointestinal tract and bladder, in endo- and exocrine glands including pancreatic b-cells and in kidney tubules.

SUMMARY OF THE INVENTION

According to the present invention it has now been found that a particular group of chemical compounds possess valuable activity as modulators of $SK_{Ca}$, $IK_{Ca}$ and/or $BK_{Ca}$ channels.

In its first aspect the invention relates to novel chemical compounds represented by the general Formula I

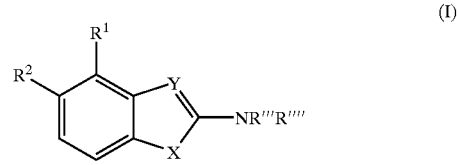

and a pharmaceutically acceptable salt or an oxide or a hydrate thereof, wherein, X and Y, independently of each another, represent an oxygen atom, a sulphur atom, or a group of the formula —NH—, in which case the dotted line represents no double bond; or a nitrogen atom, in which case the dotted line represent the location of a double bond;

R''' and R'''', independently of each another, represent hydrogen or alkyl;

$R^1$ and $R^2$, independently of each another, represent hydrogen, alkyl, alkenyl, alkynyl, cycloalkyl, amino, trihalogenmethyl, nitro, cyano, or phenyl, or a group of the formula —OR', —SR', —R'OR", —R'SR", —C(O)R', —C(S)R', —C(O)OR', —C(S)OR', —C(O)SR', —C(S)SR', —C(O)NR'(OR"), —C(S)NR'(OR"), —C(O)NR'(SR"), —C(S)NR'(SR"), —CH(CN)$_2$, —C(O)NR'$_2$, —C(S)NR'$_2$, —CH[C(O)R']$_2$, —CH[C(S)R']$_2$, —CH[C(O)OR']$_2$, —CH[C(S)OR']$_2$, —CH[C(O)SR']$_2$, —CH[C(S)SR']$_2$, CH$_2$OR', or CH$_2$SR'; or a mono- or poly-carbocyclic group, a mono- or poly-heterocyclic group, an aralkyl group, or a hetero-alkyl group, which mono- or polycyclic groups or aralkyl or hetero-alkyl groups may optionally be substituted one or more times with substituents selected from the group consisting of halogen, trihalogenmethyl, alkyl, alkenyl, alkynyl, amino, nitro, cyano, or amido, or a group of the formula —R', —OR', —SR', —R'OR", —R'SR", —C(O)R', —C(S)R', —C(O)OR', —C(S)OR', —C(O)SR', or —C(S)SR', or a phenyl or a phenoxy group, which phenyl or phenoxy groups may optionally be substituted on or more times with substituents selected from the group consisting of halogen, trihalogenmethyl, alkyl, alkenyl, alkynyl, amino, nitro, cyano, or amido, or a group of the formula —R', —OR', —SR', —R'OR", —R'SR", —C(O)R', "C(S)R', —C(O)OR', —C(S)OR', —C(O)SR', or —C(S)SR';

wherein R' and R", independently of each another, represent hydrogen, alkyl, alkenyl, alkynyl, cycloalkyl or alkoxy, or a group of the formula NR'''R'''', wherein R''' and R'''', independently of each another, represent hydrogen or alkyl; or $R^1$ and $R^2$ together form a mono- or poly-carbocyclic group, or a mono- or poly-heterocyclic group, which mono- or polycyclic groups may optionally be substituted one or more times with substituents selected from the group consisting of halogen, trihalogenmethyl, alkyl, alkenyl, alkynyl, amino, nitro, cyano, or amido, or a group of the formula —R', —OR', —SR', —R'OR", —R'SR", —C(O)R', —C(S)R', —C(O)OR', —C(S)OR', —C(O)SR', or —C(S)SR', or a phenyl or a phenoxy group, which phenyl or phenoxy groups may optionally be substituted on or more times with substituents selected from the group consisting of halogen, trihalogenmethyl, alkyl, alkenyl, alkynyl, amino, nitro, cyano, or amido, or a group of the formula —R', —OR', —SR', —R'OR", —R'SR", —C(O)R', —C(S)R', —C(O)OR', —C(S)OR', —C(O)SR', or —C(S)SR';

wherein R' and R", independently of each another, represent hydrogen, alkyl, alkenyl, alkynyl, cycloalkyl or alkoxy, or a group of the formula NR'''R'''', wherein R''' and R'''', independently of each another, represent hydrogen, or alkyl.

In a second aspect, the invention provides a pharmaceutical composition comprising a chemical compound of the invention for the treatment or alleviation of diseases or conditions responsive to modulation of SK$_{Ca}$, IK$_{Ca}$ and/or BK$_{Ca}$ channels.

The SK/IK/BK channel modulating agents of the invention are useful for the treatment or alleviation of diseases or conditions responsive to modulation of SK$_{Ca}$, IK$_{Ca}$ and/or BK$_{Ca}$ channels.

DETAILED DISCLOSURE OF THE INVENTION

According to the present invention it has now been found that a particular group of chemical compounds possess valuable activity as modulators of Sk$_{Ca}$, IK$_{Ca}$ and/or BK$_{Ca}$ channels.

SK/IK/BK Modulating Agents

In the context of this invention, chemical compounds capable of affecting SK$_{Ca}$, IK$_{Ca}$ and/or BK$_{Ca}$ channels are designated SK/IK/BK channel modulating agents. The SK/IK/BK channel modulating agents of the invention may affect the ion channels by opening (activating) the channels or by inhibiting (blocking) the channels.

The SK/IK/BK channel modulating agents of the invention show activity in concentrations below 100 μM, preferably below 10 μM, more preferred below 1 μm. In its most preferred embodiment the SK/IK/BK channel modulating agents of the invention show activity in low micromolar and the nanomolar range.

The SK/IK/BK channel modulating agents of the invention are represented by the following general Formula I

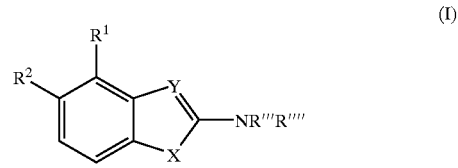

(I)

and a pharmaceutically acceptable salt or an oxide or a hydrate thereof, wherein, X and Y, independently of each another, represent an oxygen atom, a sulphur atom, or a group of the formula —NH—, in which case the dotted line represents no double bond; or a nitrogen atom, in which case the dotted line represent the location of a double bond;

R''' and R'''', independently of each another, represent hydrogen or alkyl;

$R^1$ and $R^2$, independently of each another, represent hydrogen, alkyl, alkenyl, alkynyl, cycloalkyl, amino, trihalogenmethyl, nitro, cyano, or phenyl, or a group of the formula —OR', —SR', —R'OR", —R'SR", —C(O)R', —C(S)R', —C(O)OR', —C(S)OR', —C(O)SR', —C(S)SR', —C(O)NR'(OR"), —C(S)NR'(OR"), —C(O)NR'(SR"), —C(S)NR'(SR"), —CH(CN)$_2$, —C(O)NR'$_2$, —C(S)NR'$_2$, —CH[C(O)R']$_2$, —CH[C(S)R']$_2$, —CH[C(O)OR']$_2$, —CH[C(S)OR']$_2$, —CH[C(O)SR']$_2$, —CH[C(S)SR']$_2$, CH$_2$OR', or CH$_2$SR'; or a mono- or poly-carbocyclic group, a mono- or poly-heterocyclic group, an aralkyl group, or a hetero-alkyl group, which mono- or polycyclic groups or aralkyl or hetero-alkyl groups may optionally be substituted one or more times with substituents selected from the group consisting of halogen, trihalogenmethyl, alkyl, alkenyl, alkynyl, amino, nitro, cyano, or amido, or a group of the formula —R', —OR', —SR', —R'OR", —R'SR", —C(O)R', —C(S)R', —C(O)OR', —C(S)OR', —C(O)SR', or —C(S)SR', or a phenyl or a phenoxy group, which phenyl or phenoxy groups may optionally be substituted on or more times with substituents selected from the group consisting of halogen, trihalogenmethyl, alkyl, alkenyl, alkynyl, amino, nitro, cyano, or amido, or a group of the formula —R', —OR', —SR', —R'OR", —R'SR", —C(O)R', —C(S)R', —C(O)OR', —C(S)OR', —C(O)SR', or —C(S)SR';

wherein
R' and R", independently of each another, represent hydrogen, alkyl, alkenyl, alkynyl, cycloalkyl or alkoxy, or a group of the formula NR'''R'''', wherein R''' and R'''', independently of each another, represent hydrogen or alkyl; or or $R^1$ and $R^2$ together form a mono- or polycarbocyclic group, or a mono- or poly-heterocyclic group, which mono- or polycyclic groups may optionally be substituted one or more times with substituents selected from the group consisting of halogen, trihalogenmethyl, alkyl, alkenyl, alkynyl, amino, nitro, cyano, or amido, or a group of the formula —R', —OR', —SR', —R'OR", —R'SR", —C(O)R', —C(S)R', —C(O)OR', —C(S)OR', —C(O)SR', or —C(S)SR', or a phenyl or a phenoxy group, which phenyl or phenoxy groups may optionally be substituted on or more times with substituents selected from the group consisting of halogen, trihalogenmethyl, alkyl, alkenyl, alkynyl, amino, nitro, cyano, or amido, or a group of the formula —R', —OR', —SR', —R'OR", —R'SR", —C(O)R', —C(S)R', —C(O)OR', —C(S)OR', —C(O)SR', or —C(S)SR';

wherein
R' and R", independently of each another, represent hydrogen, alkyl, alkenyl, alkynyl, cycloalkyl or alkoxy, or a group of the formula NR'''R'''', wherein R''' and R'''', independently of each another, represent hydrogen or alkyl.

In a preferred embodiment, the chemical compound of the invention is represented by the general Formula II

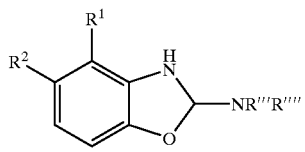

(II)

and a pharmaceutically acceptable salt or an oxide or a hydrate thereof,
wherein,
R''' and R'''' $R^1$ and $R^2$ and are as defined above.

In another preferred embodiment, the chemical compound of the invention is represented by the general Formula III

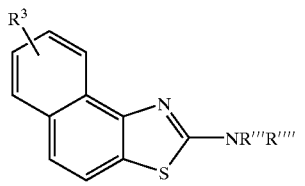

(III)

and a pharmaceutically acceptable salt or an oxide or a hydrate thereof,
wherein,
R''' and R'''' are as defined in claim 1; and
$R^3$ represents hydrogen, halogen, trihalogenmethyl, alkyl, alkenyl, alkynyl, amino, nitro, cyano, or amido, or a group of the formula —R', —OR', —SR', —R'OR", —R'SR", —C(O)R', —C(S)R', —C(O)OR', —C(S)OR', —C(O)SR', or —C(S)SR';

wherein
R' and R", independently of each another, represent hydrogen, alkyl, alkenyl, alkynyl, cycloalkyl or alkoxy, or a group of the formula NR'''R'''', wherein R''' and R'''', independently of each another, represent hydrogen or alkyl.

In a most preferred embodiment, the chemical compound of the invention is
2-Amino-4,5-dichlorobenzothiazole;
2-Amino-4,5-dimethylbenzothiazole; or
2-Amino-(5,6,7,8-tetrahydronaphto)-[1,2-d]-thiazole;
or a pharmaceutically acceptable salt or an oxide or a hydrate thereof.

Definition of Substituents

In the context of this invention halogen represents a fluorine, a chlorine, a bromine or a iodine atom. Thus, a trihalogenmethyl group represents e.g. a trifluoromethyl group and a trichloromethyl group.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl: lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In a preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, and cyclohexyl.

In the context of this invention an alkenyl group designates a carbon chain containing one or more double bonds, including di-enes, tri-enes and poly-enes. In a preferred embodiment the alkenyl group of the invention comprises of from two to eight carbon atoms ($C_{2-8}$-alkenyl), more preferred of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butenyl; 1-, 2-, 3-, 4- or 5-hexenyl, or 1,3-hexenyl, or 1,3,5-hexenyl; 1-, 2-, 3-, 4-, 5-, 6-, or 7-octenyl, or 1,3-octenyl, or 1,3,5-octenyl, or 1,3,5,7-octenyl.

In the context of this invention an alkynyl group designates a carbon chain containing one or more triple bonds, including di-ynes, tri-ynes and poly-ynes. In a preferred embodiment the alkynyl group of the invention comprises of from two to eight carbon atoms ($C_{2-8}$-alkynyl), more preferred of rom two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butynyl; 1-, 2-, 3-, 4-pentynyl, or 1,3-pentynyl; 1-, 2-, 3-, 4-, or 5-henynyl, or 1,3-hexynyl or 1,3,5-hexynyl; 1-, 2-, 3-, 4-, 5- or 6-heptynyl, or 1,3-heptynyl, or 1,3,5-heptynyl; 1-, 2-, 3-, 4-, 5-, 6- or 7-octynyl, or 1,3-octynyl, or 1,3,5-octynyl, or 1,3,5,7-octynyl.

In the context of this invention an alkoxy group designates an "alkyl-O—" group, wherein alkyl is as defined above.

In the context of this invention an acyl group designates a carboxy group (—COOH) or an alkylcarbonyl group (alkyl-CO—), wherein alkyl is as defined above. Examples of preferred acyl groups of the invention include carboxy, acetyl, and propionyl.

In the context of this invention an amido group designates a substituent of the formula R'—CO—NH— or R'—CO—N(alkyl)-, wherein R' represents hydrogen or an alkyl group as defined above. Examples of preferred amido groups include formamido, acetamido, and propionamido.

In the context of this invention an amino group may be a primary (—NH$_2$), secondary (—NH-alkyl), or tertiary (—N(alkyl)$_2$) amino group, i.e. it may be substituted once or twice with an alkyl group as defined above.

In the context of this invention a mono- or poly-carbocyclic group designates a mono- or polycyclic hydrocarbon group, which may in particular be an aromatic hydrocarbon group, i.e. a mono- or polycyclic aryl group, or a saturated hydrocarbon group, or a partially saturated hydrocarbon group. Preferred poly-carbocyclic group are the bicyclic poly-carbocyclic groups.

In the context of this invention a mono- or polycyclic aryl group designates a monocyclic or polycyclic aromatic hydrocarbon group. Examples of preferred aryl groups of the invention include phenyl, naphthyl, indenyl, azulenyl, anthracenyl, and fluorenyl.

Examples of saturated and partially saturated hydrocarbon groups include hydrocarbons like cyclopropyl, cyclobutyl, cyclopentyl, cyclohexyl, cycloheptan, cyclooctan, and cyclopenta-2,4-diene-1-ylidene, and bicyclic carbocyclic groups like norbonane and adamantane.

In the context of this invention an aralkyl group designates a mono- or polycyclic aryl group as defined above, which aryl group is attached to an alkyl group as also defined above. Examples of preferred aralkyl groups of the invention include benzyl, and phenethyl.

In the context of this invention a mono- or poly-heterocyclic group is a mono- or polycyclic compound, which holds one or more heteroatoms in its ring structure. Preferred heteroatoms include nitrogen (N), oxygen (O), and sulphur (S). One or more of the ring structures may in particular be aromatic (i.e. a heteroaryl), saturated or partially saturated. Preferred heterocyclic monocyclic groups of the invention include 5- and 6 membered heterocyclic monocyclic groups. Preferred poly-heterocyclic groups of the invention are the bicyclic heterocyclic groups.

Examples of preferred aromatic heterocyclic 5-membered monocyclic groups of the invention include furan, in particular 2- or 3-furanyl;
thiophene, in particular 2- or 3-thienyl;
pyrrole, in particular 1-, 2- or 3-pyrrolyl;
oxazole, in particular oxazol-(2-, 4- or 5-)yl;
thiazole, in particular thiazol-(2-, 4-, or 5-)yl;
imidazole, in particular imidazol-(1-, 2-, 4- or 5-)yl;
pyrazole, in particular pyrazol-(1-, 3-, 4- or 5-)yl;
isoxazole, in particular isoxazol-(3-, 4- or 5-)yl;
isothiazole, in particular isothiazol-(3-, 4- or 5-)yl;
1,2,3-oxadiazole, in particular 1,2,3-oxadiazol-(4- or 5-)yl;
1,2,4-oxadiazole, in particular 1,2,4-oxadiazol-(3- or 5-)yl;
1,2,5-oxadiazole, in particular 1,2,5-oxadiazol-(3- or 4-)yl;
1,2,3-triazole, in particular 1,2,3-triazol-(1-, 4- or 5-)yl;
1,2,4-thiadiazole, in particular 1.2,4-thiadiazol-(3- or 5-)yl;
1,2,5-thiadiazole, in particular 1,2,5-thiadiazol-(3- or 4-)yl; and
1,3,4-thiadiazole, in particular 1,3,4-thiadiazol-(2- or 5-)yl.

Examples of preferred aromatic heterocyclic 6-membered monocyclic groups of the invention include pyridine, in particular pyridin-(2-, 3- or 4-)yl;
pyridazine, in particular pyridazin-(3- or 4-)yl;
pyrimidine, in particular pyrimidin-(2-, 4- or 5-)yl;
pyrazine, in particular pyrazin-(2-, 3-, 5- or 6-)yl;
1,3,5-triazine, in particular 1,3,5-triazin-(2-, 4- or 6-)yl; and
phosphinine, in particular phosphinin-(2-, 3- or 4-)yl.

Examples of preferred saturated or partially saturated heterocyclic monocyclic 5-membered groups of the invention include 2H-pyrrole, in particular 2H-pyrrol-(2- or 3-)yl;
2-pyrroline, in particular 2-pyrrolin-(1-, 2- or 3-)yl;
3-pyrroline, in particular 3-pyrrolin-(1-, 2- or 3-)yl;
pyrrolidine, in particular pyrrolidin-(1-, 2- or 3-)yl;
1,3-dioxolan, in particular 1,3-dioxolan-(2- or 4-)yl;
imidazolidine, in particular imidazolidin-(1-, 2-, 3-, 4- or 5-)yl;
2-imidazoline, in particular 2-imidazolin-(1-, 2-, 4- or 5-)yl;
3-imidazoline, in particular 3-imidazolin-(1-, 2-, 4- or 5-)yl;
4-imidazoline, in particular 4-imidazolin-(1-, 2-, 4- or 5-)yl;
pyrazolidine, in particular pyrazolidin-(1-, 2-, 3-, 4- or 5-)yl;
2-pyrazoline, in particular 2-pyrazolin-(1-, 3-, 4- or 5-)yl; and
3-pyrazoline, in particular 3-pyrazolin-(1-, 3-, 4- or 5-)yl.

Examples of preferred saturated or partially saturated heterocyclic monocyclic 6-membered groups of the invention include 2H-pyrane, in particular 2H-pyran-(2-, 3- or 4-)yl;
4H-pyrane, in particular 4H-pyran-(2-, 3- or 4-)yl;
piperidine, in particular piperidin-(1-, 2-, 3- or 4-)yl;
1,4-dioxolane, in particular 1,4-dioxolan-(2- or 3-)yl;
morpholine, in particular morpholin-(2-, 3- or 4-)yl;
1,4-dithiane, in particular 1,4-dithian-(2- or 3-)yl;
thiomorpholine, in particular thiomorpholin-(2-, 3- or 4-)yl;
piperazine, in particular piperazin-(1-, 2-, 3- or 4-)yl;
1,3,5-trithiane, in particular 1,3,5-trithian-(2-)yl; and
1,4-oxazine, in particular 1,4-oxazin-(2-)yl.

Examples of preferred aromatic heterocyclic bi-cyclic groups of the invention include indolizine, in particular indolizin-(1-, 2-, 3-, 5-, 6-, 7- or 8)yl;
indole, in particular indol-(1-, 2-, 3-, 4-, 5-, 6- or 7)yl;
isoindole, in particular isoindol-(1-, 2-, 3-, 4-, 5-, 6- or 7-)yl;
benzo[b]furan (benzofuran), in particular benzo[b]furan-(2-, 3-, 4-, 5-, 6- or 7-)yl;
benzo[c]furan (isobenzofuran), in particular benzo[c]furan-(1-, 3-, 4-, 5-, 6- or 7-)yl;
benzo[b]thiophene (benzothiophene), in particular benzo[b]thiophen-(2-, 3-, 4-, 5-, 6- or 7-)yl;
benzo[c]thiophene (isobenzothiophene), in particular benzo[c]thiophen-(1-, 3-, 4-, 5-, 6- or 7-)yl;

benzimidazole, in particular benzimidazol-(1-, 2-, 4-, 5-, 6- or 7-)yl;

benzthiazole, in particular benzthiazol-(2-, 4-, 5-, 6- or 7-)yl;

purine, in particular purin-(2-, 6- or 8-)yl;

quinoline, in particular quinolin-(2-, 3-, 4-, 5-, 6-, 7- or 8-)yl;

isoquinoline, in particular isoquinolin-(1-, 3-, 4-, 5-, 6-, 7- or 8-)yl;

cinnoline, in particular cinnolin-(3-, 4-, 5-, 6-, 7- or 8-)yl;

phthlazine, in particular phthlazin-(1-, 4-, 5-, 6-, 7- or 8-)yl;

quinazoline, in particular quinazolin-(2-, 4-, 5-, 6-, 7- or 8-)yl;

quinoxaline, in particular quinoxalin-(2-, 3-, 5-, 6-, 7- or 8-)yl;

1,8-naphthyridine, in particular 1,8-naphthyridin-(2-, 3-, 4-, 5-, 6- or 7-)yl; and pteridine, in particular pteridin-(2-, 4-, 6- or 7-)yl.

Examples of preferred aromatic heterocyclic tri-cyclic groups of the invention include carbazole, in particular carbazol-(1-, 2-, 3-, 4-, 5-, 6-, 7-, 8- or 9-)yl;

acridine, in particular acridin-(1-, 2-, 3-, 4-, 5-, 6-, 7-, 8- or 9-)yl;

phenazine, in particular phenazin-(1-, 2-, 3-, 4-, 6-, 7-, 8- or 9-)yl;

phenothiazine, in particular phenothiazin-(1-, 2-, 3-, 4-, 6-, 7-, 8-, 9- or 10-)yl; and phenoxazine, in particular phenoxazin-(1-, 2-, 3-, 4-, 6-, 7-, 8-, 9- or 10-)yl.

Examples of preferred saturated or partially saturated heterocyclic bi-cyclic groups of the invention include indoline, in particular indolin-(1-, 2-, 3-, 4-, 5-, 6- or 7-)yl;

3H-indole, in particular 3H-indol-(2-, 3-, 4-, 5-, 6- or 7-)yl;

1H-indazole, in particular 1H-indazol-(3-, 4-, 5-, 6- or 7-)yl;

4H-quinolizine, in particular 4H-quinolizin-(1-, 2-, 3-, 4-, 6-, 7-, 8- or 9-)yl;

quinuclidine, in particular quinuclidin-(2-, 3-, 4-, 5-, 6-, 7- or 8-)yl;

isoquinuclidine, in particular isoquinuclidin-(1-, 2-, 3-, 4-, 5-, 6-, 7- or 8-)yl;

tropane, in particular tropan-(1-, 2-, 3-, 4-, 5-, 6-, 7- or 8-)yl; and nortropane, in particular nortropan-(1-, 2-, 3-, 4-, 5-, 6- or 7-)yl.

In the context of this invention a hetero-alkyl group designates a mono- or poly-heterocyclic group as described above, which heterocyclic group is attached to an alkyl group as also defined above. Examples of preferred hetero-alkyl groups of the invention include furfuryl and picolyl.

Pharmaceutically Acceptable Salts

The SK/IK/BK channel modulating agents of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention includes alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

The chemical compound of the invention may be provided in dissoluble or indissoluble forms together with a pharmaceutically acceptable solvents such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

The SK/IK/BK channel modulating agents of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in *"Enantiomers, Racemates, and Resolutions"*, John Wiley and Sons, New York (1981).

Optical active compounds can also be prepared from optical active starting materials.

Moreover, some of the chemical compounds of the invention may exist in two forms, syn- and anti-form (Z- and E-form), depending on the arrangement of the substituents around the double bond. A chemical compound of the present invention may thus be the syn- or the anti-form (Z- and E-form), or it may be a mixture hereof.

Biological Activity

According to the present invention it has now been found that the chemical compounds of the invention possess valuable activity as modulators of $SK_{Ca}$, $IK_{Ca}$ and/or $BK_{Ca}$ channels.

The SK/IK/BK channel modulating activity may be monitored using conventional electrophysiological methods such as patch-clamp techniques, or conventional spectroscopic methods such as FLIPR assay (Fluorescence Image Plate Reader; available from Molecular Devices). These methods generally comprises subjecting an $SK_{Ca}$, $IK_{Ca}$ or $BK_{Ca}$ containing cell to the action of the chemical compound of the invention, followed by monitoring the membrane potential of the $SK_{Ca}$, $IK_{Ca}$ or $BK_{Ca}$ containing cell in order to identify changes in the membrane potential caused by the action of the compound of the invention.

Based on their biological activity the compounds of the invention are considered useful for the treatment or alleviation of diseases or conditions responsive to modulation of $SK_{Ca}$, $IK_{Ca}$ and/or BK channels, including diseases or conditions like respiratory diseases such as asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic hearth disease, angina pectoris, coronary hearth disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labour, baldness, cancer, and immune suppression.

The compounds of the invention is considered particularly useful for reducing or inhibiting undesired immune-regulatory actions. In a preferred embodiment, therefore, the compounds of the may be used in the treatment or alleviation of a diseases, disorders or condition related to immune dysfunction, or in order to obtain immune suppression in an individual in need herefore.

In a more preferred embodiment, the invention relates to the use of an $IK_{Ca}$ inhibitory compound of the invention in a combination therapy with known immune-suppressants for the treatment or alleviation of a diseases, disorders or condition related to immune dysfunction, or for obtaining immune suppression Preferred immune-suppressants to combine with the compounds of the invention include Amphotericin, Busulphan, Co-trimoxazole, Chlorambucil, colony stimulating factors, corticosteroids, Cyclophosphamide, Fluconazole, folinic acid, Ganciclovir, antilymphocyte immunoglobulins, normal immunoglobulins, Methotrexate, Methylprednisolone, Octreotide, Oxpentifylline, Tacrolimus (FK506), Thalidomide, Zolimomab aritox, and the calcineurin inhibitors (protein phosphatase 2B inhibitors), in particular Cyclosporin.

Conditions which may benefit from this treatment include, but are not limited to diseases, disorders or conditions such as auto-immune diseases, e.g. Addison's disease, alopecia areata, Ankylosing spondylitis, haemolytic anemia (anemia haemolytica), pernicious anemia (anemia perniciosa), aphthae, aphthous stomatitis, arthritis, arteriosclerotic disorders, osteoarthritis, rheumatoid arthritis, aspermiogenese, asthma bronchiale, auto-immune asthma, auto-immune hemolysis, Bechet's disease, Boeck's disease, inflammatory bowel disease, Burkitt's lymphoma, Chron's disease, chorioiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, auto-immune demyelinating diseases, Dupuytren's contracture, encephalomyelitis, encephalomyelitis allergica, endophthalmia phacoanaphylactica, enteritis allergica, auto-immune enteropathy syndrome, erythema nodosum leprosum, idiopathic facial paralysis, chronic fatigue syndrome, febris rheumatica, glomerulo nephritis, Goodpasture's syndrome, Graves' disease, Hamman-Rich's disease, Hashimoto's disease, Hashimoto's thyroiditis, sudden hearing loss, sensoneural hearing loss, hepatitis chronica, Hodgkin's disease, haemoglobinuria paroxysmatica, hypogonadism, ileitis regionalis, iritis, leucopenia, leucemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granulomatosa, pancreatitis, pemphigus, pemphigus vulgaris, polyarteritis nodosa, polyarthritis chronica primaria, polymyositis, polyradiculitis acuta, psoreasis, purpura, pyoderma gangrenosum, Quervain's thyreoiditis, Reiter's syndrome, sarcoidosis, ataxic sclerosis, progressive systemic sclerosis, scleritis, sclerodermia, multiple sclerosis, sclerosis disseminate, acquired spenic atrophy, infertility due to antispermatozoan antobodies, thrombocytopenia, idiopathic thrombocytopenia purpura, thymoma, acute anterior uveitis, vitiligo, AIDS, HIV, SCID and Epstein Barr virus associated diseases such as Sjorgren's syndrome, virus (AIDS or EBV) associated B cell lymphoma, parasitic diseases such as Lesihmania, and immunosuppressed disease states such as viral infections following allograft transplantations, graft vs. Host syndrome, transplant rejection, or AIDS, cancers, chronic active hepatitis diabetes, toxic chock syndrome, food poisoning, and transplant rejection.

Pharmaceutical Compositions

In another aspect the invention provides novel pharmaceutical compositions comprising a therapeutically effective amount of a chemical compound having $SK_{Ca}$, $IK_{Ca}$ or $BK_{Ca}$ modulating activity.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers therefor, and, optionally, other therapeutic and/or prophylactic ingredients. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth;

pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co. Easton, Pa.).

A therapeutically effective dose refers to that amount of active ingredient which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions which exhibit large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner. The actual dosage depend on the nature and severity of the disease being treated and the route of administration, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method for the treatment or alleviation of diseases or disorders or conditions of living animal bodies, including humans, which diseases, disorders or conditions are responsive to modulation of $SK_{Ca}$, $IK_{Ca}$ and/or BK channels, and which method comprises administering to such a living animal body, including a human, in need thereof an effective amount of a chemical compound of the invention.

In a more preferred embodiment the disease or a disorder or a condition is a respiratory diseases such as asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic hearth disease, angina pectoris, coronary hearth disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labour, baldness, cancer, and immune suppression.

In another preferred embodiment the invention provides a method for the treatment or alleviation of diseases or disorders or conditions of living animal bodies, including humans, which diseases, disorders or conditions are responsive to an $IK_{Ca}$ inhibitory compound of the invention in a combination therapy with known immune-suppressants for the treatment or alleviation of a diseases, disorders or condition related to immune dysfunction, or for obtaining immune suppression. Preferred immune-suppressants to combine with the compounds of the invention include Amphotericin, Busulphan, Co-trimoxazole, Chlorambucil, colony stimulating factors, corticosteroids, Cyclophosphamide, Fluconazole, folinic acid, Ganciclovir, antilymphocyte immunoglobulins, normal immunoglobulins, Methotrexate, Methylprednisolone, Octreotide, Oxpentifylline, Tacrolimus (FK506), Thalidomide, Zolimomab aritox, and the calcineurin inhibitors (protein phosphatase 2B inhibitors), in particular Cyclosporin.

Conditions which may benefit from this treatment include, but are not limited to diseases, disorders or conditions such as auto-immune diseases, e.g. Addison's disease, alopecia areata, Ankylosing spondylitis, haemolytic anemia (anemia haemolytica), pernicious anemia (anemia perniciosa), aphthae, aphthous stomatitis, arthritis, arteriosclerotic disorders, osteoarthritis, rheumatoid arthritis, aspermiogenese, asthma bronchiale, auto-immune asthma, auto-immune hemolysis, Bechet's disease, Boeck's disease, inflammatory bowel disease, Burkitt's lymphoma, Chron's disease, chornoiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, auto-immune demyelinating diseases, Dupuytren's contracture, encephalomyelitis, encephalomyelitis allergica, endophthalmia phacoanaphylactica, enteritis allergica, auto-immune enteropathy syndrome, erythema nodosum leprosum, idiopathic facial paralysis, chronic fatigue syndrome, febris rheumatica, glomerulo nephritis, Goodpasture's syndrome, Graves' disease, Hamman-Rich's disease, Hashimoto's disease, Hashimoto's thyroiditis, sudden hearing loss, sensoneural hearing loss, hepatitis chronica, Hodgkin's disease, haemoglobinuria paroxysmatica, hypogonadism, ileitis regionalis, iritis, leucopenia, leucemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granulomatosa, pancreatitis, pemphigus, pemphigus vulgaris, polyarteritis nodosa, polyarthritis chronica primaria, polymyositis, polyradiculitis acuta, psoreasis, purpura, pyoderma gangrenosum, Quervain's thyreoiditis, Reiter's syndrome, sarcoidosis, ataxic sclerosis, progressive systemic sclerosis, scleritis, sclerodermia, multiple sclerosis, sclerosis disseminata, acquired spenic atrophy, infertility due to antispermatozoan antobodies, thrombocytopenia, idiopathic thrombocytopenia purpura, thymoma, acute anterior uveitis, vitiligo, AIDS, HIV, SCID and Epstein Barr virus associated diseases such as Sjorgren's syndrome, virus (AIDS or EBV) associated B cell lymphoma, parasitic diseases such as Lesihmania, and immunosuppressed disease states such as viral infections following allograft transplantations, graft vs. Host syndrome, transplant rejection, or AIDS, cancers, chronic active hepatitis diabetes, toxic chock syndrome, food poisoning, and transplant rejection.

It is at present contemplated that suitable dosage ranges are 0.1 to 1000 milligrams daily, 10–500 milligrams daily, and especially 30–100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples which are not intended to be in any way limiting to the scope of the invention as claimed.

Example 1

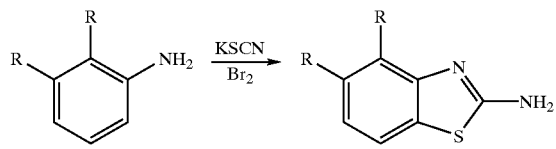

2-amino-4,5-dichlorobenzothiazole (Compound 1). To a solution of 2,3-dichloroaniline (1.0 g; 6.17 mmol) in glacial acetic acid (30 ml) was added potassium thiocyanate (3.6 g; 37 mmol) and the mixture was stirred at ambient temperature until a clear solution had formed. Bromine (0.48 ml; 9.26 mmol) was added dropwise and the reaction mixture was stirred at ambient temperature for five hours. The solvent was removed under reduced pressure and the residue was diluted with water and rendered alkaline by addition of aqueous sodium hydroxide (6M). The product was filtered off, washed with water and dried to yield the desired product quantitatively.

Mp: 126–132° C.

The following compounds were prepared analogously:

2-amino-4,5-dimethylbenzothiazole (Compound 2).

From 2,3-dimethylaniline.

Mp: 88–89° C.

2-amino-(5,6,7,8-tetrahydronaphto)-[1,2-d]-thiazole (Compound 3).

From 1-amino-5,6,7,8-tetrahydronaphtalene.

Mp: 190° (with decomposition).

Example 2

Biological Activity

In this experiment the ionic current through Intermediate-conductance $Ca^{2+}$-activated $K^+$ channels (IK channels) is recorded in the whole-cell mode of the patch-clamp technique.

Intermediate-conductance $Ca^{2+}$-activated $K^+$ channels (IK channels) have been cloned from human placenta and stably expressed in HEK293 cells.

Stable Expression of hIK in HEK293 Cells

Human IK (hIK) was excised from pT3T7 (GenBank Acc. No. N56819) using EcoR I and Not I and subcloned into the mammalian expression vector pNS1Z (NeuroSearch), a custom designed derivative of pcDNA3Zeo (InVitrogen) to give the plasmid construct pNS1Z_hIK. HEK293 tissue culture cells were grown in DMEM (Dulbecco's Modified Eagle Medium) supplemented with 10% FCS (foetal calf serum) at 37° C. in 5% $CO_2$. One day prior to transfection, $10^6$ cells were plated in a cell culture T25 flask. The following day, cells were transfected using lipofection (20 μL Lipofectamin™, Life Technologies, with 2.5 μg of the plasmid pNS1Z_hIK in a total volume of 540 μL).

The lipofection mixture was overlaid on the cells and incubated at 37° C. for 5 hours. The cells were then rinsed with regular media and grown for 72 hours in DMEM, 10% FCS at 37° C. in 5% $CO_2$. 72 hours post transfection, cells transfected with pNS1Z_hIK were selected in media supplemented with 0.25 mg/ml Zeocin. Single clones were picked and propagated in selection media until sufficient cells for freezing were available. Hereafter the cells were cultured in regular medium without selection agent. Expression of functional hIK channels was verified by patch-clamp measurements.

Whole Cell Recordings

Experiments are carried out on a patch-clamp workstation equipped with an autosampler. Cells plated on coverslips are placed in a 15 μl perfusion chamber (flowrate ~1 ml/min) mounted on a microscope equipped with Nomarski or Hoffmann optics. The microscopes are placed on vibration-free tables in grounded Faraday cages. All experiments are performed at room temperature (20–22° C.). EPC-9 patch-clamp amplifiers (HEKA-electronics, Lambrect, Germany) are connected to Macintosh computers via ITC16 interfaces. Data are stored directly on the harddisk and analysed by the IGOR software (wavemetrics, Lake Oswego, USA)

The whole-cell configuration of the patch clamp technique is applied. In short: The tip of a borosilicate pipette (resistance 2–4 MΩ) is gently (remote control system) placed on the cell membrane. Light suction results in a giga seal (pipette resistance increases to more than 1 GΩ) and the cell membrane is then ruptured by more powerful suction.

Cell capacitance is electronically compensated and the resistance between the pipette and the cell interior (the series resistance, Rs) is measured and compensated for. Usually the cell capacitance ranges from 5 to 20 pF (depending on cell size) and the series resistance is in the range 3 to 6 MΩ. Rs—as well as capacitance compensation are updated during the experiments (before each stimulus). All experiments with drifting Rs-values are discharged. Leak-subtractions are not performed.

Solutions

The extracellular (bath) solution contains (conc. in mM): 144 KCl, 0.1 CaCl$_2$, 3 MgCl$_2$, 10 HEPES (pH=7.4). The intracellular (pipette) solution has the following composition (conc. in mM): 144 KCl, 10 EGTA, 10 HEPES (pH=7.2) as well as CaCl$_2$ and MgCl$_2$ in concentrations calculated to result in a free concentration of Ca$^{2+}$ between 100 nM and 300 nM. The free concentration of Mg$^{2+}$ is calculated to be 1 mM.

Test compounds are usually dissolved as 1000 times concentrated stock solutions in DMSO and then diluted in the extracellular solution.

Quantification

After establishment of the whole-cell configuration voltage-ramps (normally −100 to +100 mV) are applied to the cell every 5 sec. Very little endogene current (<200 pA at 100 mV compared to 2–20 nA IK current) are activated under these circumstances in native HEK293 cells. A stable baseline current is obtained within a period of 100–300 seconds. Hereafter a pulseprotocol containing a trigger signal for the autosampler is applied. In this protocol 25 voltage-ramps are applied and followed by a waiting period before the next 25 voltage ramps. The autosampler collect the test compounds diluted in extracellular solution from a rack containing 10–20 testvials. A new compound is applied to the cell during each period with voltage-ramps and the chamber is washed with extracellular solution during the waiting periods.

Active compounds are quantified by calculating the change in baseline current. The baseline current is set to 100 and a value of 50 indicates that the compound has reduced the baseline current to half its value (i.e. blockers will have, values between 0 and 99 with lowest values for the strongest blockers). Activators will have values greater than 100 and a value of 200 indicates a doubling of the baseline current. Finally a value of 100 indicates that the compound does not influence the hIK current.

The results of these experiments are presented in Table 1, below.

TABLE 1

| | Ionic Currents |
|---|---|
| Test Compound | Value determined using 1 μM of the test compound |
| Compound 3 | 400 |
| Compound 2 | 130 |
| Compound 1 | 170 |

What is claimed is:

1. A method of treatment or alleviation of a disease or a disorder or a condition of a living animal body, comprising the step of administering to such a living animal body in need thereof a therapeutically effective amount of a benzothiazole compound represented by Formula IV

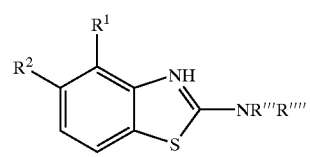

(IV)

or a pharmaceutically acceptable salt, oxide or hydrate thereof, wherein,

R''' and R'''', independently of each other, represent hydrogen or alkyl;

R$^1$ and R$^2$, independently of each other, represent hydrogen, alkyl, alkoxy, cycloalkyl, amino, halogen, trihalogenmethyl, nitro, or cyano; or R$^1$ and R$^2$, together form a mono- or poly-carbocyclic group, which may optionally be substituted one or more times with substituents selected from the group consisting of halogen, trihalogenmethyl, alkyl, alkoxy, amino, nitro, and cyano wherein said disease or a disorder or condition is urinary incontinence.

2. The method of claim 1, wherein R''' and R'''', independently of each other, represent hydrogen or lower alkyl; and R$^1$ and R$^2$, independently of each other, represent hydrogen, alkyl, alkoxy, halogen, trihalogenmethyl, nitro or cyano.

3. The method of claim 1, wherein

R''' and R'''', independently of each other, represent hydrogen or methyl; and

R$^1$ and R$^2$, independently of each other, represent hydrogen, lower alkyl, halogen or trifluoromethyl.

4. The method of claim 3, wherein the compound is

2-Amino-4,5-dichlorobenzothiazole; or

2-Amino-4,5-dimethylbenzothiazole;

or a pharmaceutically acceptable salt or an oxide or a hydrate thereof.

5. A method of treatment or alleviation of a disease or a disorder or a condition of a living animal body, comprising the step of administering to such a living animal body in need thereof a therapeutically effective amount of a benzothiazole compound represented by Formula III

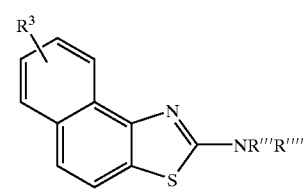

(III)

or a pharmaceutically acceptable salt thereof, wherein,

R''' and R'''' are independently of each other, represent hydrogen or alkyl; and R$^3$ represents hydrogen, halogen, trihalogenmethyl, alkyl, alkenyl, alkynyl, amino, nitro, or cyano wherein said disease or a disorder or condition is urinary incontinence.

6. A method of treatment or alleviation of a disease or a disorder or a condition of a living animal body, comprising the step of administering to such a living animal body in need thereof a therapeutically effective amount of a benzothiazole compound represented by Formula V

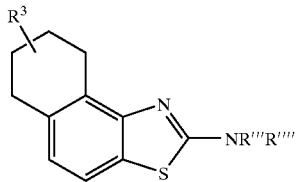
(V)

or a pharmaceutically acceptable salt thereof, wherein,
R''' and R'''', independently of each other, represent hydrogen or alkyl; and
$R^3$ represents hydrogen, halogen, trihalogenmethyl, alkyl, alkoxy, amino, nitro, or cyano
wherein said disease or a disorder or condition is urinary incontinence.

7. The method of claim 6 wherein
R''' and R'''', independently of each other, represent hydrogen or lower alkyl; and
$R^3$ represents hydrogen, lower alkyl, halogen, trihalogenmethyl, nitro or cyano.

8. The method of claim 6 wherein
R''' and R'''', independently of each other, represent hydrogen or methyl; and
$R^3$ represents hydrogen, lower alkyl, halogen or trifluoromethyl.

9. The method of claim 1, wherein the compound administered is 2-Amino-(5,6,7,8-tetrahydronaphto)-[1,2-d]-thiazole or a pharmaceutically acceptable salt or an oxide or a hydrate thereof.

10. The method according to claim 1, wherein said living animal is a human.

11. The method according to claim 5, wherein said living animal is a human.

12. The method of claim 6, wherein said living animal is a human.

* * * * *